US009345255B2

(12) United States Patent
Kindel et al.

(10) Patent No.: US 9,345,255 B2
(45) Date of Patent: May 24, 2016

(54) COMPOSITIONS

(71) Applicant: Symrise AG, Holzminden (DE)

(72) Inventors: Günter Kindel, Höxter (DE); Gerhard Krammer, Holzminden (DE); Sven Siegel, Höxter (DE)

(73) Assignee: Symrise AG, Holzminden (DE)

( * ) Notice: Subject to any disclaimer, the term of this patent is extended or adjusted under 35 U.S.C. 154(b) by 280 days.

(21) Appl. No.: 13/728,219

(22) Filed: Dec. 27, 2012

(65) Prior Publication Data

US 2013/0195773 A1    Aug. 1, 2013

(30) Foreign Application Priority Data

Jan. 30, 2012 (EP) .................................. 12153019

(51) Int. Cl.
| | |
|---|---|
| *A23L 1/22* | (2006.01) |
| *A61Q 5/00* | (2006.01) |
| *A61Q 15/00* | (2006.01) |
| *A61Q 19/04* | (2006.01) |
| *A61Q 11/00* | (2006.01) |
| *A61Q 5/12* | (2006.01) |
| *A61K 8/37* | (2006.01) |
| *A61K 8/49* | (2006.01) |
| *A61Q 17/04* | (2006.01) |
| *A61Q 19/02* | (2006.01) |
| *A23G 4/06* | (2006.01) |
| *A61K 8/34* | (2006.01) |
| *A61Q 19/00* | (2006.01) |
| *A61K 9/68* | (2006.01) |
| *A23G 4/12* | (2006.01) |
| *A61Q 5/02* | (2006.01) |
| *A61Q 19/10* | (2006.01) |
| *A23C 9/158* | (2006.01) |
| *A23G 3/36* | (2006.01) |

(52) U.S. Cl.
CPC ............... *A23L 1/22075* (2013.01); *A23G 3/36* (2013.01); *A23G 4/06* (2013.01); *A23G 4/12* (2013.01); *A61K 8/345* (2013.01); *A61K 8/37* (2013.01); *A61K 8/498* (2013.01); *A61K 8/4973* (2013.01); *A61K 9/0058* (2013.01); *A61Q 5/00* (2013.01); *A61Q 11/00* (2013.01); *A61Q 15/00* (2013.01); *A61Q 17/04* (2013.01); *A61Q 19/00* (2013.01); *A61Q 19/02* (2013.01); *A61Q 19/04* (2013.01); *A23C 9/158* (2013.01); *A23G 3/364* (2013.01); *A61Q 5/002* (2013.01); *A61Q 5/02* (2013.01); *A61Q 5/12* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 5,041,293 | A * | 8/1991 | Patel et al. ..................... 426/3 |
| 5,298,238 | A * | 3/1994 | Hussein .................. A61K 8/347 |
| | | | | 424/49 |
| 5,977,166 | A * | 11/1999 | Greenberg ..................... 514/452 |
| 6,231,900 | B1 * | 5/2001 | Hanke .............................. 426/96 |
| 2010/0273887 | A1 | 10/2010 | Machinek et al. |
| 2011/0081303 | A1 | 4/2011 | Oertling et al. |

FOREIGN PATENT DOCUMENTS

| | | |
|---|---|---|
| EP | 485170 A1 | 5/1992 |
| EP | 2014273 A1 | 1/2009 |
| EP | 2168957 A2 | 3/2010 |
| WO | 2006116436 A1 | 11/2006 |

OTHER PUBLICATIONS

Smith D. Morison and Leo Levi. Treatment of Compositional Data for the Characterization of Essential Oils. Determination of Geographical Origins of Peppermint Oils by Gas Chromatographic Analysis. Agricultural and Food Chemistry, vol. 9, No. 3, May-Jun. 1961, pp. 230-244.*
Chlodwig Franz and Johannes Novak. Chapter 3, Sources of Essential Oils in Handbook of Essential Oils, Edited by K. Husnu Can Baser and Gerhard Buchbauer. Boca Raton, FL: CRC Press, 2009, p. 68.*
European Medicines Agency (EMEA): "Public statement on the use of herbal medicinal products containing pulegone and menthofuran," Nov. 23, 2005, pp. 1-4.

* cited by examiner

*Primary Examiner* — Frederick Krass
*Assistant Examiner* — Michael P Cohen
(74) *Attorney, Agent, or Firm* — Dilworth & Barrese, LLP

(57) ABSTRACT

Compositions, comprising menthofuran and selected menthol compounds which feature improved flavor and odor properties, are provided and, in addition, the production of compositions, specifically, of emulsions with an improved storage stability.

13 Claims, No Drawings

COMPOSITIONS

AREA OF THE INVENTION

The invention relates generally to the field of cosmetics, pharmaceutics and foods and, more specifically, to compositions causing a cooling sensation on the skin or on the mucosal tissues, comprising menthofuran together with other selected menthol compounds.

STATE OF THE ART

Peppermint oil is obtained by steam distillation of peppermint (*Mentha piperita*, Lamiaceae). It is an essential oil significant in the cosmetics and pharmaceutical industries. Far more than tons are used in Germany alone each year. Similarly to mint oil, which it relates to and which is obtained from Japanese mint *Menthae arvensis aetheroleum*, peppermint oil contains, in particular, menthol (35-45%) and menthone (15-20%); in addition, it contains menthyl acetate (3-5%), neomenthol (2.5-3.5%) and isomenthol (3%). Both the essential oils and the menthol compounds (appear to) generate a cooling sensation when applied to the skin or to the mucosal tissues without influencing the body temperature; said effect is comparable to that of capsaicin, which, reversely, appears to generate a warming sensation. Menthol and some of its derivatives are, therefore, often used as analgetics or weak local anaesthetics. The effect of menthols is generally explained by the fact that the substances facilitate the transport of calcium ions into the nerve cells, which leads to an electric signal that is percepted by the brain as a cooling sensation.

Another important component of the various mint oils is menthofuran,

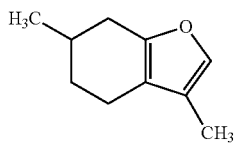

which has, besides very desirable profiles (sweet, hay/mint-like) also undesired odour and flavour profiles (odour: poignant and pungent; flavour: slightly bitter, tarry and unpleasant). Due to these undesired profiles it is often required, particularly in pharmaceutical applications, to reduce or completely remove this component, for example, by vacuum destillation, which is, naturally, complex and expensive.

In addition, menthofuran has a second feature which appears only in formulations. In fact, it can be observed that compositions comprising menthol compounds and which are present as emulsions show a decreasing stability—particularly at higher temperatures—depending on the menthofuran content. Oil droplets will not separate in a commercially available sun lotion, which contains peppermint oil in a quantity of about 1% by weight—which does not only serve as a fragrance, but also as a "cooling" component—when stored at 30° C. over a period of 24 hours, if the menthofuran content in peppermint oil is below 1% by weight. However, initial clouding is observed already after 12 hours at a menthofuran content of, for example, 2.5% by weight and a slight creaming of the formulation after 24 hours. Even though this effect does not have any effect on the effectivity of the sun protection, the consumer considers it to be a hidden fault of the product and equates it with a "cheap" formulation.

The object of the present invention, therefore, was to provide compositions comprising menthofuran together with a second substance, which is capable to mask or soften the unpleasant odour or flavour profiles such that only the desired odour and flavour profiles of menthofuran would be percepted. Thus it would no longer be necessary to remove this aroma component, which is valuable in itself. In addition, the additives should be able to balance the negative features of menthofuran, particularly in context with the emulsion stability of compositions comprising menthol compounds.

DESCRIPTION OF THE INVENTION

A first subject of the invention relates to compositions generating a cooling effect, comprising
(a) menthofuran and
(b) menthol compounds corresponding to formulas (I), (II) and/or (III)

(I)

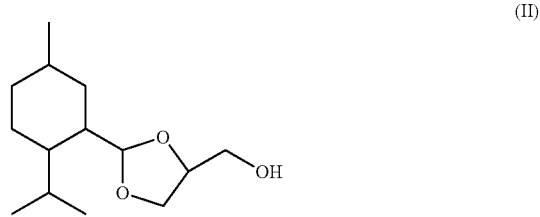

(II)

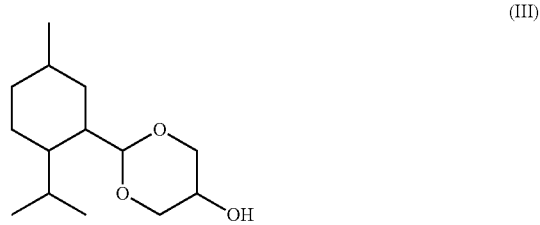

(III)

in which X represents —OY or —COZ and Y represents the following groups:
(i) a linear or branched alkyl or hydroxyl alkyl radical containing 1 to 6 carbon atoms or an allyl radical;
(ii) a hydroxy or dihydroxyalkyl radical containing 1 to 6 carbon atoms;
(iii) a radical —OCR$^1$;
(iv) a radical —OCO(M)OH;
(v) a radical —OCO—S
(vi) a radical —OC(CH$_2$)$_n$COR$^2$
wherein
M represents a linear or branched alkyl and/or alkenyl radical containing 1 to 10, preferably, 1 to 4 carbon atoms;
S represents a carbohydrate radical containing 5 to 12 carbon atoms, preferably, a fructose, a glucose or a sucrose radical;
n stands for 0 or for numbers of 1 to 6, preferably, of 2 to 3;
R$^1$ represents a linear or branched alkyl- or hydroxyl alkyl radical containing 1 to 6, preferably, 1 to 2 carbon atoms or an allyl radical;

$R^2$ represents a hydroxyl radical or a radical —$NR^3R^4$;

$R^3$ and $R^4$, independently of one another, represent hydrogen or a linear or branched alkyl or hydroxyl alkyl radical containing 1 to 6, preferably, 1 to 2 carbon atoms, while Z represents the following groups:

(vii) a radical $NR^5R^6$ or (viii) a radical $NHR^7$ wherein $R^5$ and $R^6$, independently of one another, represent hydrogen or a linear or branched alkyl or hydroxyl alkyl radical containing 1 to 6, preferably, 1 to 2 carbon atoms, a phenyl radical or an alkoxyphenyl radical containing 1 to 6, preferably, 1 to 2 carbon atoms in the alkoxy radical;

$R^7$ represents a radical —$(CH_2)_n COOR^8$;

$R^8$ represents a linear or branched alkyl or hydroxy alkyl radical containing 1 to 6, preferably, 1 to 2 carbon atoms, and n stands for 0 or for numbers of 1 to 10, preferably, of 1 to 4.

Surprisingly it was found that the addition of the above mentioned selected menthol compounds did not only completely compensate the undesired odour and flavour profiles of menthofuran. Thus it is not necessary any more to remove it in a complex manner; in addition, the additives solve the problem of the insufficient emulsion stability. It has proved to be particularly advantageous to use one part of menthol compounds, specifically menthone glycerol acetal/ketal, in a ratio to three parts of menthofuran, wherein the effects are already clearly visible when the content of menthol compounds in peppermint oil exceeds 1% by weight. A concentration of from about 3 to about 15% by weight of the menthol compounds, specifically, of menthone glycerol acetal/ketal in peppermint oil is particularly effective.

During the examination of the sensory features of oral and dental care products it was also found by accident that mixtures of menthofuran and the particular menthol compounds—in contrast to conventional products, for example, untreated peppermint oil—reduces the solubility of hydroxylapatite and inhibits the growth of crystals such that said compositions also counteract the demineralization of enamel and prevent the formation of calculus.

Menthol Compounds

Menthol compounds, which can be used within the meaning of the invention, are, for example, selected from the group consisting of menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamat, monomethyl succinate (FEMA GRAS 3810), monomethyl glutamate (FEMA GRAS 4006), menthoxy-1,2-propanediol (FEMA GRAS 3784), menthoxy-2-methyl-1,2-propandiol (FEMA GRAS 3849) and the menthan carboxylic acid esters and amides WS-3, WS-4, WS-5, WS-12, WS-14 and WS-30 and mixtures thereof.

[1] FEMA stands for "Flavor and Extracts Manufacturers Association" and GRAS is defined as "Generally Regarded As Safe". A FEMA GRAS designation means that the substance designated such has been tested according to standard methods and is considered to be toxicologically safe.

Although menthol has been known as a cooling substance for many decades and is indispensible in a large number of uses to this date, this substance certainly has quite a number of disadvantages: it is volatile, has a pungent odour and a bitter flavour. In higher concentrations it is no longer percepted to be pleasantly cooling, but to be pungent and burning. Finally, menthol cannot be formulated arbitrarily, as it may interact with other chemical components. This has led to the development of the most diverse menthol compounds, of which a number within the meaning of the invention is capable to neutralize the negative features of menthofuran. All these substances are commercially available and can be produced according to the conventional methods of organic chemistry.

A first important representative of the substances forming component (b) is monomenthyl succinate (FEMA GRAS 3810), which was patented as a substance already in 1963 for Brown & Williamson Tobacco Corp. (U.S. Pat. No. 3,111, 127). As a cooling agent it is subject matter of U.S. Pat. No. 5,725,865 and U.S. Pat. No. 5,843,466 (V. Mane Fils). Both the succinate and also the analogue monomethyl glutarate (FEMA GRAS 4006) are important representatives of monomenthyl esters on the basis of di- and poly-carboxylic acids:

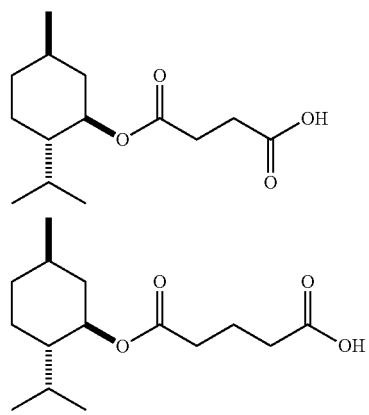

Examples of applications of these substances are available, for example, in the publications of WO 2003 043431 (Unilever) or EP 1332772 A1 (IFF).

The next important group of preferred menthol compounds within the meaning of the invention comprises carbonate esters of menthol and polyols such as, for example, glycols, glycerol or carbohydrates such as, for example, menthol ethylenglycol carbonate (FEMA GRAS 3805=Frescolat® MGC), menthol propylenglycol carbonate (FEMA GRAS 3784=Frescolat® MPC), menthol 2-methyl-1,2-propandiol carbonate (FEMA GRAS 3849) or the corresponding sugar derivatives:

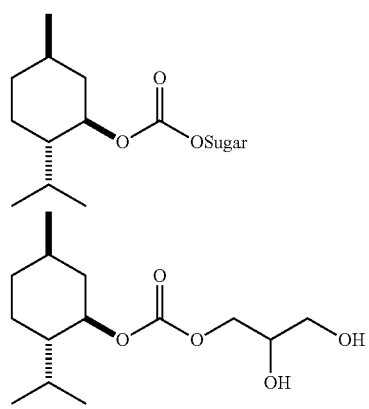

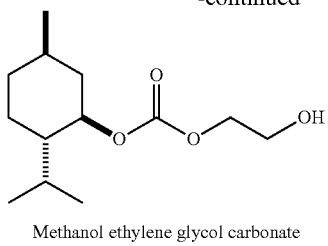

Methanol ethylene glycol carbonate

The use of such substances as a cooling agent for cigarettes is, for example, subject of U.S. Pat. No. 3,419,543 (Mold et al.) of 1968; their use as a physiological cooling agent is claimed in DE 4226043 A1 (H&R).

The menthol compounds menthyl lactate (FEMA GRAS 3748=Frescolat® ML) and, particularly, menthone glyceryl acetal (FEMA GRAS 3807) or, respectively, menthone glyceryl ketal (FEMA GRAS 3808), which is marketed under the trade name Frescolat® MAG are preferred within the meaning of the invention.

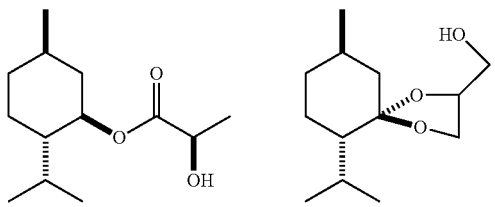

The first structure is obtained by esterification of lactic acid with menthol, the latter by acetalisation of menthone with glycerol (cf. DE 2608226 A1, H&R). This group of compounds also includes 3-(I-Menthoxy)-1,2,propandiol, which is also known as Cooling Agent 10 (FEMA GRAS 3784, cf. U.S. Pat. No. 6,328,982, TIC), and 3-(I-Menthoxy)-2-methyl-1,2,propandiol (FEMA GRAS 3849), which contains an additional methyl group.

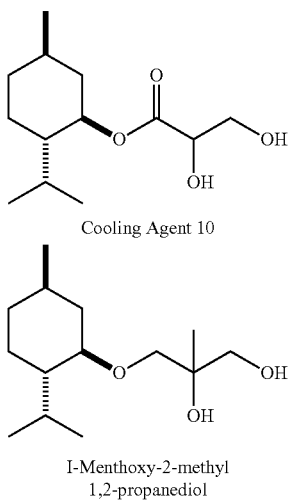

Cooling Agent 10

I-Menthoxy-2-methyl 1,2-propanediol 3-(I-Menthoxy)-1,2,propandiol is produced, for example, according to the following scheme on the basis of menthol (cf. U.S. Pat. No. 4,459,425, Takagaso):

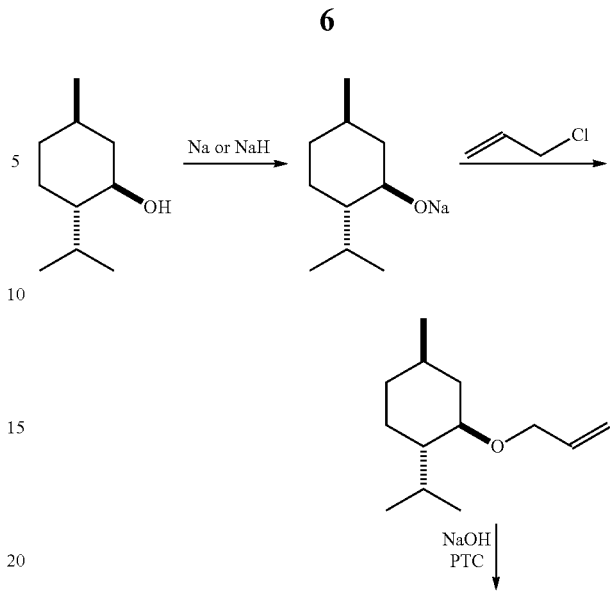

Alternative routes, in which menthol is reacted with epichlorohydrin in the first step, are described in U.S. Pat. No. 6,407,293 and U.S. Pat. No. 6,515,188 (Takagaso). An overview of preferred menthol compounds which are characterized by a CO bond is provided in the following:

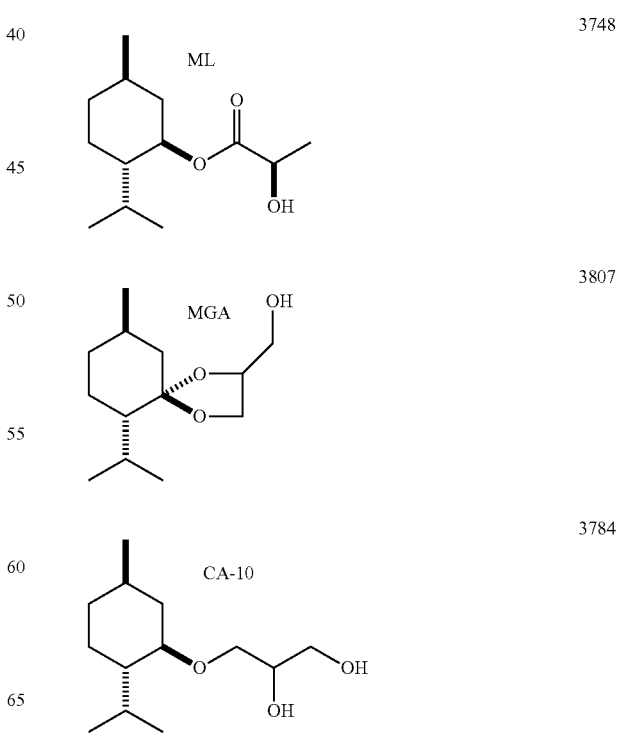

-continued

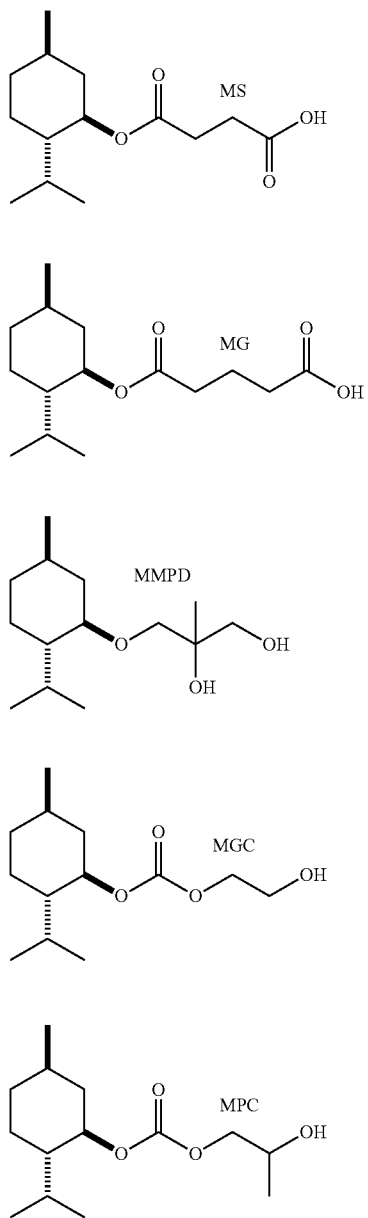

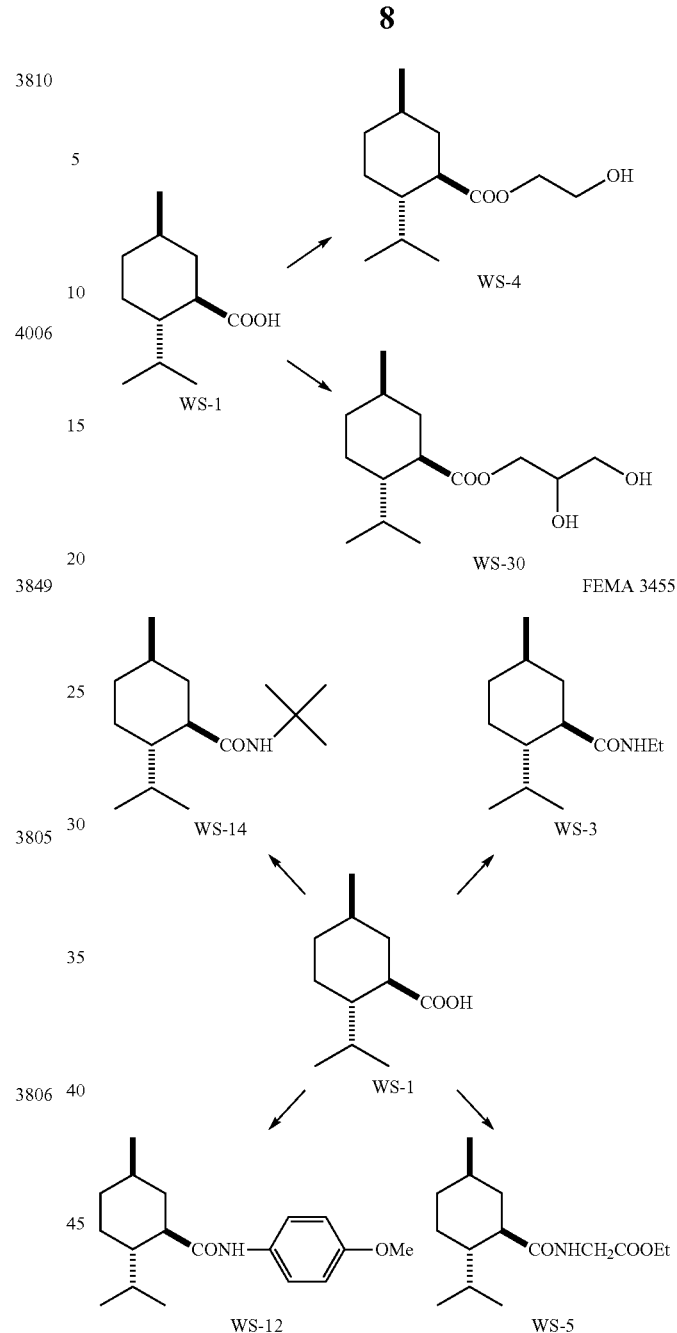

Among these substances, the following substances have proven to be particularly advantageous: menthone glyceryl acetal/ketal and menthyl lactate as well as menthol ethylene glycol carbonate or, respectively, menthol propylene glycol carbonate, which are sold by the applicant under the trade names Frescolat® MGA, Frescolat® ML, Frescolat® MGC and Frescolat® MPC.

Menthol compounds, which have a C—C bond in the 3-position were developed for the first time in the 1970ies. Out of these, also a number of representatives within the meaning of the invention may be used. These substances are generally referred to as WS types. A menthol derivative forms the base body, in which the hydroxyl group is replaced by a carboxyl group (WS-1). All other WS types are derived from this structure such as, for example, the preferred species within the meaning of the invention WS-3, WS-4, WS-5, WS-12, WS-14 and WS-30. The two following illustrations show the synthesis paths:

The esters derived from WS-1 are described, for example, in U.S. Pat. No. 4,157,384, and the corresponding N-substituted amides in J. Soc. Cosmet. Chem. S. 185-200 (1978).

In another preferred embodiment of the invention, the compositions may comprise as component (c) cosmetic additives, selected from the group consisting of surfactants, oil bodies, emulsifiers, pearlizing waxes, stabilizers, thickeners, superfatty agents, stabilizers, polymers, silicone compounds, fats, waxes, lecithines, phospholipids, UV protection factors, moisturizers, biogenic actives, antioxidants, deodorants, antiperspirants, anti-dandruff agents, film formers, swelling agents, insect repellants, self-tanning agents, tyrosine inhibitors (depigmenting agents), hydrotropes, solubilizers, preservatives, perfume oils and dyes and mixtures thereof. Said compositions, particularly when present as emulsions, are characterized by an improved storability.

The preparations according to the invention may comprise components (a) and (b) in the weight ratio of from 0.1:99 to 99.9:1, preferably, of from 10:90 to 90:10, more preferably of from 25:75 to 75:25, and particularly preferably of from 40:60 to 60:40. Components (a+b) and (c) may be comprised in the weight ratio of from 0.01:99.9 to 2:98, preferably, of from 0.5:99.5 to 1.5:98.5 and most preferably, about 1:99.

INDUSTRIAL APPLICATION

Cosmetic and/or Pharmaceutical Compositions

A further subject matter of the present invention relates to cosmetic compositions, comprising
(a) menthofuran,
(b) menthol compounds corresponding to the formulas (I), (II) and/or (III) and
(c) a carrier approved for use in cosmetic applications.

The cosmetic products include, preferably, skin care products, hair care products, body care products, sun protection agents and oral and dental care products. Particularly advantageous are compositions which are present as emulsions, microemulsions or PIT emulsions.

A further subject matter of the present invention relates to pharmaceutical compositions, comprising
(a) menthofuran,
(b) menthol compounds corresponding to the formulas (I), (II) and/or (III) and
(c) a carrier approved for use in pharmaceutical applications for treatment of cold symptoms, wherein the characterizing feature of the invention is that a therapeutic application is performed.

The pharmaceutic products include, preferably, lozenges, cold drops, syrups, cold balms and cold sprays to relieve cold symptoms.

The cosmetic or pharmaceutic carriers are, preferably, selected from the group consisting of water, alcohols containing 2 to 6 carbon atoms, polyols containing 1 to 10 carbon atoms and 2 to 4 hydroxyl groups and oil bodies. Particularly preferably are, besides water, ethanol, isopropyl alcohol, ethylene glycol, propylene glycol, glycerol, trimethylolpropane, pentaerythritol and esters of linear or branched, saturated, and, particularly, unsaturated fatty acids containing 6 to 22, and, preferably, 8 to 18 carbon atoms with alcohols containing 1 to 6 carbon atoms.

The cosmetic and/or pharmaceutical compositions according to the invention may contain components (a) and (b) in the weight ratio of from 0.1:99 to 99.9:1, preferably, of from 10:90 to 90:10, more preferably of from 25:75 to 75:25, and most preferably of from 40:60 to 60:40. Components (a+b) and (c) may be contained in the weight ratio of from 0.01:99.9 to 2:98, preferably of from 0.5:99.5 to 1.5:98.5, and specifically of about 1:99.

The cosmetic and/or pharmaceutical compositions may comprise other typical auxiliaries and additives, such as mild surfactants, oil bodies, emulsifiers, pearlizing waxes, consistency factors, thickeners, superfatty agents, stabilizers, polymers, silicone compounds, fats, waxes, lecithins, phospholipids, UV protection factors, moisturizers, biogenic actives, antioxidants, repellants, self-tanning agents, tyrosine inhibitors (depigmenting agents), hydrotropes, solubilizers, preservatives, perfume oils and dyes and the like.

Surfactants

Suitable surfactants may include anionic, nonionic, cationic and/or amphoteric or zwitterionic surfactants. Their proportion in the active gents amounts to usually of from about 1 to 70, preferably, of from about 5 to 50, and more preferably of from about 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formulas, optionally partly oxidized alk(en)yl oligoglycosides or glucoronic acid derivatives, fatty acid-N-alkyl glucamides, protein hydrolyzates (more particularly wheat-based plant products) polyol fatty acid esters, sugar esters, sorbitan esters, and amine oxides. If the non-ionic surfactants contain polyglycol ether chains, they may have a conventional distribution although they preferably have a narrow-range homolog distribution. Typical examples of cationic surfactants are quaternary ammonium compounds, such as, for example, dimethyl distearyl ammonium chloride and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Typical examples of particularly suitable mild, i.e. particularly skin-compatible surfactants are fatty alcohol polyglycol ether sulfates, monoglyceride sulphate, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, the latter, preferably, wheat-based proteins.

Oil Bodies

Suitable oil bodies are, for example, Guerbet alcohols based on fatty alcohols having 6 to 18, preferably 8 to 10, carbon atoms, esters of linear C6-C22-fatty acids with linear or branched C6-C22-fatty alcohols or esters of branched C6-C 13-carboxylic acids with linear or branched C6-C 22-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear C6-C22-fatty acids with branched alcohols, in particular 2-ethylhexanol, esters of C18-C38-alkyl hydroxy carboxylic acids with linear or branched C6-C22-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on C6-C10-fatty acids, liquid mono-/di-/triglyceride mixtures based on C6-C18-fatty acids, esters of C6-C22-fatty alcohols and/or Guerbet alcohols with aromatic carboxylic acids, in particular benzoic acid, esters of C2-C12-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched C6-C22-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched C6-C22-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Suitable emulsifiers are, for example, non-ionogenic surfactants selected from at least one of the following groups:
  addition products of 2 to 30 mol ethylene oxide and/or 0 to 5 mol propylene oxide onto linear C8-22 fatty alcohols, onto C12-22 fatty acids and onto alkyl phenols containing 8 to 15 carbon atoms in the alkyl group and alkyl amines containing 8 to 22 carbon atoms in the alkyl group;
  alkyl and/or alkenyl oligoglycosides containing 8 to 22 carbon atoms in the alk(en)yl group and ethoxylated analogs thereof
  addition products of 1 to 15 mol ethylene oxide onto castor oil and/or hydrogenated castor oil;
  addition products of 15 to 60 mol ethylene oxide onto castor oil and/or hydrogenated castor oil;
  partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;
  partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;
  mixed esters of pentaerythritol, fatty acids, citric acid and fatty alcohol and/or mixed esters of fatty acids containing 6 to 22 carbon atoms, methyl glucose and polyols, preferably glycerol or polyglycerol.
  mono-, di- and trialkyl phosphates and mono-, di and/or tri-PEG-alkyl phosphates and salts thereof;
  wool wax alcohols;
  polysiloxane/polyalkyl polyether copolymere and corresponding derivatives;
  block copolymers, for example Polyethyleneglycol-30 Dipolyhydroxystearate;
  polymer emulsifiers, for example, Pemulen types (TR-1, TR-2) of Goodrich or Cosmedia® SP of Cognis;
  polyalkylene glycoles and
  glycerine carbonat.

Particularly suitable emulsifiers are described in more detail as follows:

(a) Alkoxylates

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene onto glycerol are known as lipid layer enhancers for cosmetic compositions.

(b) Alkyl- and/or Alkenyl Oligo Glycosides

Alkyl and/or alkenyl oligoglycosides, production and their use are known from the state of the art. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

(c) Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

(d) Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

(e) Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-4 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like.

(f) Anionic Emulsifiers

Typical anionic emulsifiers are aliphatic C12-22 fatty acids, such as palmitic acid, stearic acid or behenic acid, for example, and C12-22 dicarboxylic acids such as azelaic acid or sebacic acid, for example.

(g) Amphoteric and Cationic Emulsifiers

Other suitable emulsifiers are zwitterionic surfactants. Zwitterionic surfactants are surface-active compounds, which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a C8/18 alkyl or acyl group, contain at least one free amino group and at least one —COOH— or —SO3H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkyl-aminopropionic acids and alkylaminoacetic acids containing around 8 to 18 carbon atoms in the alkyl group. Particularly preferred ampholytic surfactants are N-cocoalkylamino-propionate, cocoacylaminoethyl aminopropionate and C12/18 acyl sarcosine. Eventually, also cationic surfactants are suitable emulsifiers, wherein the esterquat type, preferably, methylquaternized difatty acid triethanolamine ester salts are particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat®(BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacryl-amide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

UV Protection Factors

UV protection factors are, for example, organic substances (light filters) which are liquid or crystalline at room temperature and which are capable of absorbing ultraviolet radiation and of releasing the energy absorbed in the form of longer-wave radiation, for example, heat. UV protection protection factors are usually present in amounts of 0.1 to 5 and, preferably, 0.2 to 1% by weight. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomethyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester triazine derivatives such as, for example, 2,4,6-trianilino-(p-carbo-2'-ethyl-1'-hexyloxy)-1,3,5-triazine and Octyl Triazone, or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives

Suitable water-soluble substances are:

2-phenylbenzimidazole-5-sulfonic acid and alkali metal, alkaline earth metal, ammonium, alkylammonium, alkanolammonium and glucammonium salts thereof;

1H-benzimidazole-4,6-disulfonic acid, 2,2'-(1,4-phenylene) bis-, disodium salt (Neo Heliopan® AP)

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789), 2-(4-Diethylamino-2-hydroxybenzoyl)-benzoic acid hexylester (Uvinul® A Plus), 1-phenyl-3-(4'-isopropylphenyl)-propane-1,3-dione and enamine compounds. The UV-A and UV-B filters may of course also be used in the form of mixtures. Particularly favourable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805

(Degussa) and Eusolex® T2000, Eusolex® T, Eusolex® T-ECO, Eusolex® T-S, Eusolex® T-Aqua, Eusolex® T-45D (all from Merck), Uvinul TiO2 (BASF). Suitable hydrophobic coating materials are, above all, silicones and, among these, especially trialkoxyoctylsilanes or simethicones. So-called micro- or nanopigments are preferably used in sun protection products. Micronized zinc oxide such as, for example, Z-COTE® or Z-COTE HP1® is preferably used.

Moisturizers

Moisturizers are added to improve the sensory properties of the composition as well as to regulate skin hydration. At the same time, the stability in cold temperatures of the compositions according to the invention is increased, particularly in emulsions. Moisturizers are typically present in quantities of 0.1 to 15% by weight, preferably, 1 to 10% by weight, and more particularly 5 to 10% by weight.

Suitable moisturizers according to the invention are a.o. amino acids, pyrrolidone carbonic acid, lactic acid and its salts, lactitol, urea and urea derivatives, ureic acid, glucosamine, creatinine, hydrolysis products of collagen, chitosan or chitosan salts/-derivatives, and in particular polyols and polyol derivatives (e.g. ethylene glycol, propylene glycol, butylene glycol, erythrite, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugar and sugar derivatives (a.o. fructose, glucose, maltose, maltitol, mannite, inosite, sorbite, sorbityl silandiol, sucrose, trehalose, xylose, xylit, glucuronic acid and its salts), ethoxylated sorbitol (Sorbeth-6, Sorbeth-20, Sorbeth-30, Sorbeth-40), honey and hydrogenated honey, hydrogenated starch hydrolysates, as well as mixtures of hydrogenated wheat protein and PEG-20-acetate copolymers. Particularly preferred moisturizers according to the invention are glycerine, diglycerine, triglycerine and butylene glycol.

Biogenic Agents and Antioxidants

Biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Antioxidants interrupt the photo-chemical reaction chain which is triggered as soon as UV radiation enters the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to ⊠ mol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate), and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (for example ZnO, ZnSO4), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids.

Deodorants and Anti-Microbial Agents

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

(a) Germ Inhibitors

Suitable germ inhibitors are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

(b) Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

(c) Odour Adsorbers

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, everynl, iraldein gamma, phenylacetic acid, geranyl acetate, benzyl acetate, rose oxide, romilat, irotyl and floramat alone or in mixtures.

(d) Antiperspirant Active Agents

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol:
Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine. Oil-soluble and water-soluble auxiliaries typically encountered in antiperspirants may also be present in relatively small amounts. Oil-soluble auxiliaries such as these include, for example:

inflammation-inhibiting, skin-protecting or pleasant-smelling essential oils,
synthetic skin-protecting agents and/or
oil-soluble perfume oils.
Common water-soluble auxiliaries are, for example, preservatives, water-soluble fragrances, pH value adjustment agents, for example, buffer mixtures, water-soluble thickeners, for example, water-soluble natural or synthetic polymers such as, for example, Xanthan-Gum, hydroxyethyl cellulose, polyvinyl pyrrolidone or high molecular polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Anti-Dandruff Agents

Suitable antidandruff agents are Pirocton Olamin (1-hydroxy-4-methyl-6-(2,4,4-trimethyl-pentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers or swelling agents can be found in R. Lochhead's review in Cosm. Toil. 108, 95 (1993).

Insect Repellents

Suitable insect repellents are N,N-diethyl-m-toluamide, pentane-1,2-diol and ethyl butyl acetylaminopropionate. A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Ingredients for Oral and Dental Care Products

In general, tooth pastes and tooth cremes are usually understood to be gel or pasty compositions of water, thickeners, moisturizers, abrasives or cleaning agents, surfactants, sweeteners, flavours, deodorizing agents and agents against oral and dental conditions. Tooth pastes according to the invention may comprise any common cleaning agents such as, for example, chalk, dicalcium phosphate, insoluble sodium metaphosphate, aluminium silicates, calcium pyrophosphate, fine-particle synthetic resins, silicic acids, aluminium oxide and aluminiumoxide trihydrate.

Particularly suitable cleaning agents for the tooth pastes according to the invention are, preferably, fine-particle silicic acid xerogels, silicic acid hydrogels, precipitation silicic acids, aluminiumoxide trihydrate and fine-particle alpha-aluminiumoxide or mixtures of said cleaning agents in quantities of 15 to 40% by weight of the tooth paste. Suitable moisturizers are, preferably, low-molecular polyethylene glycols, glycerol, sorbit or mixtures of these products in quantities of up to 50% by weight. Suitable known thickeners are the thickening, fine-particle gel silicic acids and hydrocolloids such as, for example, carboxymethyl cellulose, hydroxyethyl cellulose, hydroxypropyl guar, hydroxyethyl starch, polyvinyl pyrrolidone, high-molecular polyethylene glycol, vegetable gums such as gum tragacanth, agar-agar, carrageen moss, gum arabicum, xantham gum and carboxyvinyl polymers (for example, Carbopol® types). In addition to the mixtures of menthofuran and menthol compounds, the oral and dental care products may comprise, in particular, surface-active substances, preferably, anionic and nonionic high-foam surfactants like the substances mentioned above, particularly, alkylether sulphate salts, alkyl polyglucosides and their mixtures.

Further common additives to tooth pastes are:
preservatives and anti-bacterial agents such as, for example, p-hydroxybenzoic acid methyl/ethyl or propyl esters, sodium sorbate, sodium benzoate, bromochlorophene, phenyl salicylic acid esters, thymol and the like;
anticalculus agents, such as organophosphates, for example 1-hydroxyethane-1,1-diphosphonic acid, 1-phosphonopropane-1,2,3-tricarboxylic acid and others, which are known for example, from U.S. Pat. No. 3,488,419, DE 2224430 A1 and DE 2343196 A1;
other anti-cariogenic substances such as, for example, sodium fluoride, sodium monofluorophosphate, tin fluoride;
sweeteners such as, for example saccharin sodium, sodium cyclamate, sucrose, lactose, maltose, fructose or Apartam®, (L-Aspartyl-L-phenylalanin-methylester), Stevia extracts and their sweetening compounds, particularly, rebaudiosides;
additional aromas such as, for example, eucalyptus oil, aniseed oil, fennel oil, caraway oil, methyl acetate, cinnamon aldehyde, anethole, vanillin, thymol and mixtures of these and other natural and synthetic aromas;
pigments such as, for example, titan dioxide;
dyes;
buffer substances such as, for example, primary, secondary or tertiary alkali phosphates or citric acid/sodium citrate;
wound-healing and inflammation-inhibiting substances such as, for example, allantoin, urea, azulene, chamomile active ingredients and derivatives of acetylsalicylic acid.

A preferred form of embodiment of the cosmetic compositions are tooth pastes in form of an aqueous, pasty dispersion, comprising polishing agents, moisturizers, viscosity regulators and, if necessary, further common components, as well as the mixture of mentho furane and menthol compounds in amounts from 0.5 to 2% by weight.

For mouthwashs, a combination with hydroalcoholic solutions of differing degrees of essential oils, emulsifiers, astringent and toning drug extracts, calculus-inhibiting agents, anti-bacterial additives and flavour correctants is quite possible. Another preferred embodiment of the invention is a mouthwash in form of an aqueous or a hydroalcoholic solution, comprising the mixture of menthofuran and menthol compounds in amounts of from 0.5 to 2% by weight. In mouthwash compositions, which are thinned before application, higher concentrations may yield sufficient effects corresponding to the intended thinning ratio.

Hydrotropes

In addition, hydrotropes, for example ethanol, isopropyl alcohol or polyols, may be used to improve flow behaviour. These substances mostly correspond to the carriers described above. Suitable polyols preferably contain 2 to 15 carbon atoms and at least two hydroxyl groups. The polyols may contain other functional groups, more especially amino groups, or may be modified with nitrogen. Typical examples are
glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example, sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the known silver compounds referred to as Surfacine® and the other classes of compounds listed in Appendix 6, Parts A and B of the Kosmetikverordnung ("Cosmetics Directive")

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, *costus*, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds, which, together, produce an agreeable perfume. Other suitable perfume oils are essential oils of relatively low volatility, which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Dyes

Suitable dyes are any of the substances suitable and approved for cosmetic purposes as listed, for example, in the publication "Kosmetische Färbemittel" of the Farbstoff-kommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are usually used in concentrations of from 0.001 to 0.1% by weight, based on the total mixture.

The total amount of auxiliaries and additives may be from 1 to 50, preferably, from 5 to 40% by weight—based on the agents. The agents may be produced by known cold or hot processes; preferably, the phase inversion temperature method is applied.

Food Compositions

A further subject matter of the invention relates to food compositions, comprising,
(a) menthofuran,
(b) menthol compounds corresponding to the formulas (I), (II) and/or (III) and
(c) a carrier approved for nutritional purposes.

The carriers may be selected from the group consisting of water, ethanol and glycerol.

The food compositions are, preferably, beverages, milk products, bakery products and, particularly, chewing gums and bonbons.

The compositions according to the invention may comprise the components (a) and (b) in the weight ratio of from 0.1:99 to 99.9:1, preferably, of from 10:90 to 90:10, more preferably, of from 25:75 to 75:25, and most preferably of from 40:60 to 60:40. The components (a+b) and (c) may be comprised in the weight ratio of from 0.01:99.9 to 2:98, preferably of from 0.5:99.5 to 1.5:98.5, and particularly about 1:99.

Chewing Gums

The preferred food compositions, comprising the mixtures of menthofuran and the menthol compounds as flavouring substances are chewing gums. These products typically contain a water-insoluble and a water-soluble component.

Water-Insoluble Base

The water-insoluble base, which is also known as "gum base", typically comprises natural or synthetic elastomers, resins, fats and oils, plasticizers and softeners, fillers, dyes and optionally waxes. The base normally makes up 5 to 95% by weight, preferably 10 to 50% by weight, and more particularly 20 to 35% by weight of the composition as a whole. In one typical form of embodiment of the invention, the base consists of 20 to 60% by weight synthetic elastomers, 0 to 30% by weight natural elastomers, 5 to 55% by weight plasticizers, 4 to 35% by weight fillers, and small amounts of additives, such as dyes, antioxidants and the like, with the proviso that they are soluble in water at best in small amounts.

Suitable synthetic elastomers are, for example, polyisobutylenes with average molecular weights (as measured by GPC) of 10,000 to 100,000 and preferably 50,000 to 80,000, isobutylen/isoprene copolymers ("butyl elastomers"), styrene/butadiene copolymers (styrene:butadiene ratio, for example, 1:3 to 3:1), polyvinyl acetates with average molecular weights (as measured by GPC) of 2,000 to 90,000 and preferably 10,000 to 65,000, polyisoprenes, poly-ethylenes, vinyl acetate/vinyl laurate copolymers and mixtures thereof. Examples of suitable natural elastomers are rubbers such as, for example, smoked or liquid latex or guayuls, and natural gums, such as jelutong, lechi caspi, perillo, sorva, massaranduba balata, massaranduba chocolate, nispero, rosindinba, chicle, gutta hang kang and mixtures thereof. The choice of the synthetic and natural elastomers and their mixing ratios essentially depends on whether or not bubbles are to be produced with the chewing gums ("bubble gums"). Elastomer mixtures containing jelutong, chicle, sorva and massanduraba are preferably used.

In most cases, the elastomers are too hard or lack plasticity for satisfactory processing, so it has been found to be of advantage to use special plasticizers which, of course, must also satisfy in particular all requirements relating to acceptability as food additives. In this respect, suitable plasticizers are, above all, esters of resin acids, for example, esters of lower aliphatic alcohols or polyols with completely or partly hydrogenated, monomeric or oligomeric resin acids. In particular, the methyl, glycerol or pentaerythritol esters or mixtures thereof are used for this purpose. Alternatively, terpene resins, which may be derived from α-pinene, β-pinene, δ-limonene or mixtures thereof, could also be used.

Suitable fillers or texturizers are magnesium or calcium carbonate, ground pumice stone, silicates, especially magnesium or aluminium silicates, clays, aluminium oxides, talcum, titanium dioxide, mono-, di- and tricalcium phosphate and cellulose polymers.

Suitable emulsifiers are tallow, hydrogenated tallow, hydrogenated or partly hydrogenated vegetable oils, cocoa butter, partial glycerides, lecithin, triacetin and saturated or unsaturated fatty acids containing 6 to 22 and preferably 12 to 18 carbon atoms and mixtures thereof.

Suitable dyes and whiteners are, for example, the FD & C types, plant and fruit extracts permitted for colouring foods and titanium dioxide.

The gum bases may contain waxes, or may be wax-free; examples of wax-free compositions can be found inter alia in U.S. Pat. No. 5,286,500, to the disclosure of which reference is hereby specifically made.

Water-Soluble Components

In addition to the water-insoluble gum base, chewing gum compositions regularly contain a water-soluble component, which is formed, for example, by softeners, sweeteners, fillers, flavours, flavour enhancers, emulsifiers, dyes, acidifiers, antioxidants and the like, with the proviso in this case that the constituents have at least adequate solubility in water. Accordingly, individual constituents may belong both to the water-insoluble phase and to the water-soluble phase, depending on the water solubility of the special representatives. However, combinations may also be used, for example, a combination of a water-soluble and a water-insoluble emulsifier, in which case the individual representatives are present in different phases. The water-insoluble component usually makes up 5 to 95% by weight and preferably 20 to 80% by weight of the preparation.

Water-soluble softeners or plasticizers are added to the chewing gum compositions to improve chewability and the chewing feel and are present in the mixtures in quantities of typically 0.5 to 15% by weight. Typical examples are glycerol, lecithin and aqueous solutions of sorbitol, hydrogenated starch hydrolysates or corn syrup.

Suitable sweeteners are both sugar-containing or sugar-free compounds which are used in quantities of 5 to 95% by weight, preferably in quantities of 20 to 80% b weight and more particularly in quantities of 30 to 60% by weight, based on the chewing gum composition. Typical saccharide sweeteners are sucrose, dextrose, maltose, dextrin, dried invert sugar, fructose, fructose, levulose, galactose, corn syrup and mixtures thereof. Suitable sugar substitutes are sorbitol, mannitol, xylitol, hydrogenated starch hydrolysates, maltitol and mixtures thereof. Further suitable additives are so-called high-intensity artificial sweeteners (HIAS) such as, for example, sucralose, aspartame, acesulfam salts, alitam, saccharin and saccharin salts, cyclamic acid and salts thereof, glycyrrhicins, dihydrochalcones, thaumatin, monellin and the like either individually or in the form of mixtures. The hydrophobic HIAS, which are the subject of International Patent Application WO 2002 091849 A1 (Wrigleys), are also particularly effective, as well as Stevia extracts and their active ingredients, particularly, Ribeaudiosid A. The quantity in which these substances are used is primarily determined by their intensity and is typically in the range from 0.02 to 8% by weight.

Fillers are particularly suitable for the production of low-calorie chewing gums and may be selected, for example, from polydextrose, raftilose, raftilin, fructo-oligosaccharides (NutraFlora), palatinose oligosaaccharides, guar gum hydrolysates (Sun Fiber) and dextrins.

The choice in flavours is virtually unlimited and is not critical to the essence of the invention. They normally make up 0.1 to 15% by weight and preferably 0.2 to 5% by weight of the chewing gum composition. Suitable flavours are, for example, essential oils, synthetic aromas and the like, such as, for example, aniseed oil, Japanese anise oil, caraway oil, eucalyptus oil, fennel oil, citrus oil, wintergreen oil, clove oil, menthol and the like, such as used, for example, in oral and dental care products.

The chewing gums may additionally contain auxiliaries and additives, which are suitable, for example, for dental care, more particularly for controlling plaque and gingivitis, such as, for example, chlorhexidine, CPC or triclosan. They may also contain pH adjusters (for example, buffer or urea), anti-caries agents (for example, phosphates or fluorides), biogenic agents (antibodies, enzymes, caffeine, plant extracts), providing these substances are permitted in foods and do not undesirably interact with one another.

Capsules

The compositions of menthofuran and the menthol compounds alone or the ready-made cosmetic, pharmaceutical and food compositions may also be present in encapsulated form. Besides the common macrocapsules on the basis of gelatine, so-called microcapsules or nanocapsules are suitable. "Microcapsules" are understood by the expert to be spherical aggregates with a diameter of about 0.0001 to about 5 mm and, preferably, 0.005 to 0.5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, molten waxes are absorbed in a matrix ("microsponge") which, as microparticles, may be additionally coated with film-forming polymers.

According to a third method, particles are covered with alternating layers of differently charged polyelectrolytes ("layer-by-layer" method). The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone. Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicerin C30 (lactose, microcrystalline cellulose, hydroxypropylmethyl cellulose), Kobo Glycospheres (modified starch, fatty acid esters, phospholipids), Softspheres (modified agar agar), Kuhs Probiol Nanospheres (phospholipids), Primaspheres and Primasponges (chitosan, alginates) and Primasys (phospholipids).

Particularly interesting for the encapsulation of compositions for cosmetic applications are coacervates of cationic polymers, particularly of chitosan, with anionic polymers, specifically alginates. Chitosan microcapsules and processes for their production are the subject of International Patent Applications WO 2001/01926, WO 2001/01927, WO 2001/01928, WO 2001/01929 [Cognis].

Gel Formers

Microcapsules often contain active agents which are dissolved or dispersed in a gel phase. Preferred gel formers for the purposes of the invention are substances which are capable of forming gels in aqueous solution at temperatures above 40° C. Typical examples of such gel formers are heteropolysaccharides and proteins. Preferred thermogelling heteropolysaccharides are agaroses which may be present in the form of the agar agar obtainable from red algae, even together with up to 30% by weight of non-gel-forming agaropectins. The principal constituent of agaroses are linear polysaccharides of D-galactose and 3,6-anhydro-L-galactose with alternate β-1,3- and β-1,4-glycosidic bonds. The heteropolysaccharides preferably have a molecular weight of 110,000 to 160,000 and are both odorless and tasteless. Suitable alternatives are pectins, xanthans (including xanthan gum) and mixtures thereof. Other preferred types are those which—in 1% by weight aqueous solution—still form gels that do not melt below 80° C. and solidify again above 40° C. Examples from the group of thermogelling proteins are the various gelatine types.

Cationic Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat®(BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol. Preferably, chitosan is used as encapsulation material. Chitosans are biopolymers which belong to the group of hydrocolloids. Chemically, they are partly deacetylated chitins varying in molecular weight which contain the idealized monomer unit:

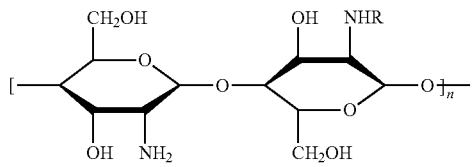

In contrast to most hydrocolloids, which are negatively charged at biological pH values, chitosans are cationic biopolymers under these conditions. The positively charged chitosans are capable of interacting with positively charged surfaces and are therefore used in cosmetic hair-care and body-care products and pharmaceutical preparations. Chitosans are produced from chitin, preferably from the shell residues of crustaceans which are available in large quantities as inexpensive raw materials. Normally, the chitin is first deproteinized by addition of bases, demineralized by addition of mineral acids and, finally, deacetylated by addition of strong bases in a process described for the first time by Hackmann et al., the molecular weights being distributed over a broad spectrum. Preferred types are those which have an average molecular weight of 10,000 to 500,000 dalton or 800,000 to 1,200,000 dalton and/or a Brookfield viscosity (1% by weight in glycolic acid) below 5,000 mPas, a degree of deacetylation of 80 to 88% and an ash content of less than 0.3% by weight.

In the interests of better solubility in water, the chitosans are generally used in the form of their salts, preferably as glycolates.

Anionic Polymers

The function of the anionic polymers is to form membranes with the cationic ones. Preferred anionic polymers are salts of alginic acids. The alginic acid is a mixture of carboxyl-containing polysaccharides with the following idealized monomer unit:

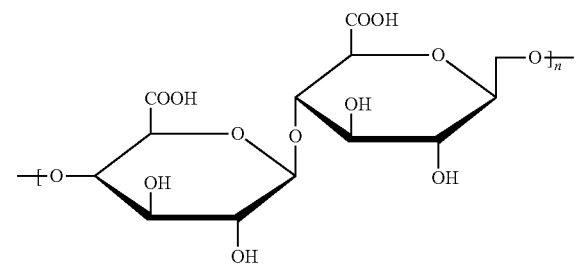

The average molecular weight of the alginic acid or the alginates is in the range from 150,000 to 250,000. Salts of alginic acid and complete and partial neutralization products thereof are understood in particular to be the alkali metal salts, preferably sodium alginate ("algin") and the ammonium and alkaline earth metal salts. Mixed alginates, for example, sodium/magnesium or sodium/calcium alginates, are particularly preferred. In an alternative embodiment of the invention, however, anionic chitosan derivatives, for example, carboxylation and above all succinylation products, are also suitable for this purpose. Alternatively, poly(meth) acrylates with average molecular weights of 5,000 to 50,000 dalton and the various carboxymethyl celluloses may also be used. Instead of the anionic polymers, anionic surfactants or low molecular weight inorganic salts, such as, pyrophosphates, for example, may also be used for forming the membrane.

Encapsulation

To produce the microcapsules, a 1 to 10 and preferably, 2 to 5% by weight aqueous solution of the gel former, preferably agar-agar, is normally prepared and heated under reflux. A second aqueous solution containing the cationic polymer, preferably chitosan in quantities of 0.1 to 2 and preferably 0.25 to 0.5% by weight and the active principles in quantities of 0.1 to 25 and preferably 0.25 to 10% by weight is added in the boiling heat, preferably at 80 to 100° C.; this mixture is called the matrix. Accordingly, the charging of the microcapsules with active substances may also comprise 0.1 to 25% by weight, based on the weight of the capsules. If desired, water-insoluble constituents, for example, inorganic pigments, may be added at this stage to adjust viscosity, generally in the form of aqueous or aqueous/alcoholic dispersions. In addition, to emulsify or disperse the active substances, it can be useful to add emulsifiers and/or solubilisers to the matrix. After its preparation from gel former, cationic polymer and active principles, the matrix may optionally be very finely dispersed in an oil phase with intensive shearing in order to produce small particles in the subsequent encapsulation process. It has proved to be particularly advantageous in this regard to heat the matrix to temperatures in the range from 40 to 60° C. while the oil phase is cooled to 10 to 20° C. The actual encapsulation, i.e. formation of the membrane by contacting the cationic polymer in the matrix with the anionic polymers, takes place in the last, again compulsory step. To this end, it is advisable to treat the matrix optionally dispersed in the oil phase with an aqueous ca. 1 to 50 and preferably 10 to 15% by weight aqueous solution of the anionic polymer at a temperature of 40 to 100° C. and preferably at a temperature of 50 to 600 and, if necessary, to remove the oil phase either at the same time or afterwards. The resulting aqueous preparations generally have a microcapsule content of 1 to 10% by weight. In some cases, it can be of advantage for the solution of the polymers to contain other ingredients, for example, emulsifiers or preservatives. After filtration, microcapsules with a mean diameter of preferably about 0.01 to 1 mm are obtained. It is advisable to sieve the capsules to ensure a uniform size distribution. The microcapsules thus obtained may have any shape within production-related limits, but are preferably substantially spherical. Alternatively, the anionic polymers may also be used for the preparation of the matrix and encapsulation may be carried out with the cationic polymers.

In an alternative process, encapsulation can also be performed by exclusively using cationic polymers, in the process of which their feature of coagulating at pH values above the pKs value is used.

In a second alternative process for the production of the microcapsules according to the invention, an o/w emulsion containing an effective quantity of emulsifier besides the oil component, water and the active principles is first prepared. To produce the matrix, a suitable quantity of an aqueous anionic polymer solution is added to this preparation with vigorous stirring. The membrane is formed by adding the chitosan solution. The entire process preferably takes place in the mildly acidic range at pH 3 to 4. If necessary, the pH is adjusted by adding mineral acid. After formation of the membrane, the pH is raised to 5 to 6, for example, by adding triethanolamine or another base. This results in an increase in viscosity which can be supported by adding other thickeners such as, for example, polysaccharides, more particularly xanthan gum, guar-guar, agar-agar, alginates and tyloses, carboxymethyl cellulose and hydroxyethyl and hydroxypropyl cellulose, also relatively high molecular weight polyethylene glycol mono- and diesters of fatty acids, polyacrylates and polyacrylamides. Finally, the microcapsules are removed from the aqueous phase by, for example decantation, filtration or centrifuging.

In a third, alternative, procedure, microcapsules are formed around a preferably solid, for example, crystalline, core, by coating it with oppositely charged polyelectrolytes in layers. In this context it is referred to European Patent EP 1064088 B1 (Max-Planck Gesellschaft).

Use of the Compositions

Lastly, the invention relates to the use of mixtures, comprising
(a) menthofuran and
(b) menthol compounds corresponding to the formulas (I), (II) and/or (III)
for the production of cosmetic compositions, pharmaceutical compositions and food compositions.

EXAMPLES

Examples 1 to 7, Comparison Examples V1 to V4

Chewing gum materials, consisting of 20% by weight polyisobutylene (MW 60.000), 51% by weight sorbitol, 5% by weight mannitol, 8% by weight glycerol, 8.2% by weight a 1:1 mixture of lycasine and glycerol, 0.2% by weight lecithine (ad 99.5% by weight water) were produced and reacted with 0.5% by weight different synthetic aroma composition each. Subsequently, the chewing gum materials were sensorily evaluated by a panel of 5 trained people on a scale from 1 (barely perceivable) to 10 (dominant). Table 1 shows the composition of the aroma components as well as the evaluation of the individual flavour and odour profiles (the mean value of the evaluations is indicated in each case). Examples 1 to 7 are according to the invention and examples V1 to V4 serve comparison purposes.

TABLE 1

Sensory evaluation of chewing gums depending on the aroma component

| Composition | V1 | 1 | 2 | 3 | 4 | 5 | 6 | 7 | V2 | V3 | V4 |
|---|---|---|---|---|---|---|---|---|---|---|---|
| Aroma component | | | | | | | | | | | |
| Menthol | | | | | | 60 | | | | | |
| Menthone | | | | | | 25 | | | | | |
| Methylacetat | | | | | | 5 | | | | | |
| Neomenthol | 4 | 3 | 3 | 3 | 3 | 3 | 3 | 3 | 3 | 3 | 3 |
| Isomenthol | 4 | 3 | 3 | 3 | 3 | 3 | 3 | 3 | 3 | 3 | 3 |
| Menthofuran | 2 | 2 | 2 | 2 | 2 | 2 | 2 | 2 | 2 | 2 | 2 |
| Methyl Lactate | — | 2 | — | — | — | — | — | — | — | — | — |
| Menthone Glyceryl Acetal | — | — | 2 | — | — | — | — | — | — | — | — |
| Menthol Ethylen Glycol Carbonate | — | — | — | 2 | — | — | — | — | — | — | — |
| Menthol Propylen Glycol Carbonate | — | — | — | — | 2 | — | — | — | — | — | — |
| Menthyl Succinate | — | — | — | — | — | 2 | — | — | — | — | — |
| Menthyl Glutamate | — | — | — | — | — | — | 2 | — | — | — | — |
| WS-5 | — | — | — | — | — | — | — | 2 | — | — | — |
| WS-1 | — | — | — | — | — | — | — | — | 2 | — | — |
| Isopulegol | — | — | — | — | — | — | — | — | — | 2 | — |
| Thymol | — | — | — | — | — | — | — | — | — | — | 2 |
| Water | | | | | Ad 100 | | | | | | |
| Sensory Evaluation | | | | | | | | | | | |
| Sweet | 4 | 5 | 6 | 6 | 6 | 6 | 6 | 6 | 4 | 4 | 4 |
| Hay/mint | 4 | 6 | 8 | 7 | 7 | 7 | 7 | 7 | 5 | 5 | 5 |
| Poignant | 8 | 5 | 4 | 5 | 5 | 5 | 6 | 5 | 7 | 8 | 8 |
| Pungent | 8 | 5 | 4 | 5 | 5 | 5 | 6 | 5 | 7 | 8 | 8 |
| Bitter | 8 | 5 | 4 | 5 | 4 | 4 | 6 | 6 | 7 | 8 | 8 |
| Tarry | 7 | 3 | 1 | 3 | 3 | 3 | 3 | 3 | 6 | 6 | 6 |

The control formulation V1 contained a mixture of menthol compounds corresponding to a classic peppermint oil before vacuum distillation. The menthofuran content of 2% by weight had the effect that the sweet and minty odour of the oil was barely perceptible, but masked by pungent flavours; in addition, the product clearly tasted bitter and very much like tar. In examples according to the invention 1 to 7, a part of neomenthol and isomenthol was exchanged for synthetic menthol compounds while the proportion of menthofuran remained unchanged. All these formulations clearly scored higher in the sensory evaluation, in particular, the formulations tasted more sweet than bitter, the tarry flavour was almost completely masked, and the unpleasant poignant and pungent odour was perceptively reduced. In doing so, the use of menthone glyceryl acetal was particularly advantageous. In the same manner, various other menthol compounds were used in comparison experiments V2 to V4. Although these caused a slight improvement of the sensory features, the results were still unsatisfactory at the end, i.e., the chewing gum compositions were evaluated to be negative and not to be suitable for marketing at the end.

Examples 8 to 14, Comparison Examples V5 to V8

Various clear O/W sun screen emulsions were produced according to the PIT method by mixing the components as shown in Table 2:

TABLE 2

Composition of O/W sun screen lotions

| Component | Commercial product | Amount [% by weight] |
|---|---|---|
| Polyglyceryl-2-Polyhydroxystearate (and) Lauryl Glucosides (and) Glycerin | Eumulgin ® VL 75 | 2.5 |
| Glyceryl Stearate | Cutina ® GMS | 2.0 |
| Cetearyl Alcohol | Lanette ® O | 4.0 |
| PVP/Hexadecen Copolymer | Antaron ® V216 | 3.0 |
| Cocoglycerides | Myritol ® 818 | 6.0 |
| Oleyl Erucate | Cetiol ® J600 | 3.0 |
| Dicaprylyl Ether | Cetiol ® OE | 5.0 |
| Mineral Oil | | 2.0 |
| Bisabolol | | 1.2 |
| Tocopherol | Copherol ® F 1300 | 1.0 |
| Octocrylene | Neo Heliopan ® 303 | 4.0 |
| Isoamyl-p-methoxycinnamat | Neo Heliopan ® E 1000 | 2.0 |
| Octyl-methoycinnamate | Neo Heliopan ® AV | 3.0 |
| Octyl Triazon | Uvinul ® T15 | 1.0 |
| Aroma mixture | | 0.5 |
| Glycerol | | 5.0 |
| Water | | Ad 100 |

The sun screen lotions only differ with respect to the composition of the aroma mixture, in which conventional peppermint oil was recreated on the one hand, and proportions of neomenthol and isomenthol were exchanged for various synthetic menthol compounds on the other.

After production, the lotions were bottled into transparent PET bottles and stored at 30° C. Subsequently, the lotions were evaluated with respect to their appearance after 12, 24 and 48 h. In doing so, (+)=unchanged; (#) slight formation of droplets and (−) separation of oil droplets on the surface and slight discolouring to a yellowish tone. The results are shown in Table 3. As before, examples 8 to 14 are according to the invention and examples V5 to V8 serve comparison purposes.

TABLE 3

Evaluation of storage stability of O/W sun screen lotions depending on the aroma components

| Composition | V5 | 8 | 9 | 10 | 11 | 12 | 13 | 14 | V6 | V7 | V8 |
|---|---|---|---|---|---|---|---|---|---|---|---|
| Aroma components | | | | | | | | | | | |
| Menthol | 60 | | | | | | | | | | |
| Menthone | 25 | | | | | | | | | | |
| Methylacetat | | | | | | 5 | | | | | |
| Neomenthol | 4 | 3 | 3 | 3 | 3 | 3 | 3 | 3 | 3 | 3 | 3 |
| Isomenthol | 4 | 3 | 3 | 3 | 3 | 3 | 3 | 3 | 3 | 3 | 3 |
| Menthofuran | 2 | 2 | 2 | 2 | 2 | 2 | 2 | 2 | 2 | 2 | 2 |
| Methyl Lactate | — | 2 | — | — | — | — | — | — | — | — | — |
| Menthone Glyceryl Acetal | — | — | 2 | — | — | — | — | — | — | — | — |
| Menthol Ethylen Glycol Carbonate | — | — | — | 2 | — | — | — | — | — | — | — |
| Menthol Propylen Glycol Carbonate | — | — | — | — | 2 | — | — | — | — | — | — |
| Menthyl Succinate | — | — | — | — | — | 2 | — | — | — | — | — |
| Menthyl Glutamate | — | — | — | — | — | — | 2 | — | — | — | — |
| WS-5 | — | — | — | — | — | — | — | 2 | — | — | — |
| WS-1 | — | — | — | — | — | — | — | — | 2 | — | — |
| Isopulegol | — | — | — | — | — | — | — | — | — | 2 | — |
| Thymol | — | — | — | — | — | — | — | — | — | — | 2 |
| Water | | | | | Ad 100 | | | | | | |
| Evaluation | | | | | | | | | | | |
| After 12 h | # | + | + | + | + | + | + | + | + | + | + |
| After 24 h | # | + | + | + | + | + | + | + | # | # | # |
| After 48 h | − | + | + | # | # | + | # | + | − | − | − |

Control formulation V4, again, contained a mixture of menthol compounds corresponding to a classic peppermint oil before vacuum distillation. The menthofuran content of 2% by weight had the effect that oil droplets separated very quickly in the product, and the content easily discoloured to a yellowish tone. In examples according to the invention 8 to 14 a proportion of the neomenthols and isomenthol was exchanged for synthetic menthol compounds while the proportion of menthofuran remained unchanged. All those formulations showed a clearly better evaluation when optically evaluated. Thereby, the use of Menthone Glyceryl Acetal was particularly advantageous: the corresponding formulations proved to be completely storage stable. In the same manner, various other menthol compounds were used in comparison experiments V5 to V8. Although these had a slight effect on improving storage stability, the results were quite as bad in the end as in the case of peppermint oil recreation.

The following tables show numerous formulation examples of cosmetic, pharmaceutical and food compositions.

TABLE 4

Examples of cosmetic compositions (water, preservatives ad 100% by weight)

| Composition (INCI) | 1 | 2 | 3 | 4 | 5 | 6 | 7 | 8 | 9 | 10 |
|---|---|---|---|---|---|---|---|---|---|---|
| Texapon ® NSO Sodium Laureth Sulfate | — | — | — | — | — | — | 38.0 | 38.0 | 25.0 | — |
| Texapon ® SB 3 Disodium Laureth Sulfosuccinate | — | — | — | — | — | — | — | — | 10.0 | — |
| Plantacare ® 818 Coco Glucosides | — | — | — | — | — | — | 7.0 | 7.0 | 6.0 | — |
| Plantacare ® PS 10 Sodium Laureth Sulfate (and) Coco Glucosides | — | — | — | — | — | — | — | — | — | 16.0 |
| Dehyton ® PK 45 Cocamidopropyl Betaine | — | — | — | — | — | — | — | — | 10.0 | — |
| Dehyquart ® A Cetrimonium Chloride | 2.0 | 2.0 | 2.0 | 2.0 | 4.0 | 4.0 | — | — | — | — |

TABLE 4-continued

Examples of cosmetic compositions (water, preservatives ad 100% by weight)

| | | | | | | | | | | |
|---|---|---|---|---|---|---|---|---|---|---|
| Dehyquart ® 80 Dicocoylmethylethoxymonium Methosulfate (and) Propylenglycol | 1.2 | 1.2 | 1.2 | 1.2 | 0.6 | 0.6 | — | — | — | — |
| Eumulgin ® B2 Ceteareth-20 | 0.8 | 0.8 | — | 0.8 | — | 1.0 | — | — | — | — |
| Eumulgin ® VL 75 Lauryl Glucoside (and) Polyglyceryl-2 Polyhydroxystearate (and) Glycerin | — | — | 0.8 | — | 0.8 | — | — | — | — | — |
| Lanette ® O Cetearyl Alcohol | 2.5 | 2.5 | 2.5 | 2.5 | 3.0 | 2.5 | — | — | — | — |
| Cutina ® GMS Glyceryl Stearate | 0.5 | 0.5 | 0.5 | 0.5 | 0.5 | 1.0 | — | — | — | — |
| Cetiol ® HE PEG-7 Glyceryl Cocoate | 1.0 | — | — | — | — | — | — | — | 1.0 | — |
| Cetiol ® PGL Hexyldecanol (and) Hexyldecyl Laurate | — | 1.0 | — | — | 1.0 | — | — | — | — | — |
| Cetiol ® V Decyl Oleate | — | — | — | 1.0 | — | — | — | — | — | — |
| Eutanol ® G Octyldodecanol | — | — | 1.0 | — | 1.0 | — | — | — | — | — |
| Nutrilan ® Keratin W Hydrolyzed Keratin | — | — | — | 2.0 | — | — | — | — | — | — |
| Lamesoft ® LMG Glyceryl Laurate (and) Potassium Cocoyl Hydrolyzed Collagen | — | — | — | — | — | — | 3.0 | 2.0 | 4.0 | — |
| Euperlan ® PK 3000 AM Glycol Distearate (and) Laureth-4 (and) Cocamidopropyl Betaine | — | — | — | — | — | — | — | 3.0 | 5.0 | 5.0 |
| Generol ® 122 N Soja Sterol | — | — | — | — | 1.0 | 1.0 | — | — | — | — |
| Menthofuran/Frescolat MGA (1:1) | 0.3 | 0.3 | 0.3 | 0.3 | 0.3 | 0.3 | 0.3 | 0.3 | 0.3 | 0.3 |
| Hydagen ® CMF Chitosan | 1.0 | 1.0 | 1.0 | 1.0 | 1.0 | 1.0 | 1.0 | 1.0 | 1.0 | 1.0 |
| Copherol ® 1250 Tocopherol Acetate | — | — | 0.1 | 0.1 | — | — | — | — | — | — |
| Arlypon ® F Laureth-2 | — | — | — | — | — | — | 3.0 | 3.0 | 1.0 | — |
| Sodium Chloride | — | — | — | — | — | — | — | 1.5 | — | 1.5 |

| Composition (INCI) | 11 | 12 | 13 | 14 | 15 | 16 | 17 | 18 | 19 | 20 |
|---|---|---|---|---|---|---|---|---|---|---|
| Texapon ® NSO Sodium Laureth Sulfate | 20.0 | 20.0 | 12.4 | — | 25.0 | 11.0 | — | — | — | — |
| Texapon ® K 14 S Sodium Myreth Sulfate | — | — | — | — | — | — | — | — | 11.0 | 23.0 |
| Texapon ® SB 3 Disodium Laureth Sulfosuccinate | — | — | — | — | — | 7.0 | — | — | — | — |
| Plantacare ® 818 Coco Glucosides | 5.0 | 5.0 | 4.0 | — | — | — | — | — | 6.0 | 4.0 |
| Plantacare ® 2000 Decyl Glucoside | — | — | — | — | 5.0 | 4.0 | — | — | — | — |
| Plantacare ® PS 10 Sodium Laureth Sulfate (and) Coco Glucosides | — | — | — | 40.0 | — | — | 16.0 | 17.0 | — | — |
| Dehyton ® PK 45 Cocamidopropyl Betaine | 20.0 | 20.0 | — | — | 8.0 | — | — | — | — | 7.0 |
| Eumulgin ® B1 Ceteareth-12 | — | — | — | — | 1.0 | — | — | — | — | — |
| Eumulgin ® B2 Ceteareth-20 | — | — | — | 1.0 | — | — | — | — | — | — |
| Lameform ® TGI Polyglyceryl-3 Isostearate | — | — | — | 4.0 | — | — | — | — | — | — |
| Dehymuls ® PGPH Polyglyceryl-2 Dipolyhydroxystearate | — | — | 1.0 | — | — | — | — | — | — | — |
| Monomuls ® 90-L 12 Glyceryl Laurate | — | — | — | — | — | — | — | — | 1.0 | 1.0 |
| Cetiol ® HE PEG-7 Glyceryl Cocoate | — | 0.2 | — | — | — | — | — | — | — | — |

TABLE 4-continued

Examples of cosmetic compositions (water, preservatives ad 100% by weight)

| | | | | | | | | | | |
|---|---|---|---|---|---|---|---|---|---|---|
| Eutanol ® G Octyldodecanol | — | — | — | 3.0 | — | — | — | — | — | — |
| Nutrilan ® Keratin W Hydrolyzed Keratin | — | — | — | — | — | — | — | — | 2.0 | 2.0 |
| Nutrilan ® I Hydrolyzed Collagen | 1.0 | — | — | — | — | 2.0 | — | 2.0 | — | — |
| Lamesoft ® LMG Glyceryl Laurate (and) Potassium Cocoyl Hydrolyzed Collagen | — | — | — | — | — | — | — | — | 1.0 | — |
| Lamesoft ® 156 Hydrogenated Tallow Gyceride (and) Potassium Cocoyl Hydrolyzed Collagen | — | — | — | — | — | — | — | — | — | 5.0 |
| Gluadin ® WK Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM Glycol Distearate (and) Laureth-4 (and) Cocamidopropyl Betaine | 5.0 | 3.0 | 4.0 | — | — | — | — | 3.0 | 3.0 | — |
| Arlypon ® F Laureth-2 | 2.6 | 1.6 | — | 1.0 | 1.5 | — | — | — | — | — |
| Menthofuran/Frescolat MGA (1:1) | 0.3 | 0.3 | 0.3 | 0.3 | 0.3 | 0.3 | 0.3 | 0.3 | 0.3 | 0.3 |
| Hydagen ® CMF Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |
| Glycerin (86% by weight) | — | 5.0 | — | — | — | — | — | 1.0 | 3.0 | — |

| Composition (INCI) | 21 | 22 | 23 | 24 | 25 | 26 | 27 | 28 | 29 | 30 |
|---|---|---|---|---|---|---|---|---|---|---|
| Texapon ® NSO Sodium Laureth Sulfate | — | 30.0 | 30.0 | — | 25.0 | — | — | — | — | — |
| Plantacare ® 818 Coco Glucosides | — | 10.0 | — | — | 20.0 | — | — | — | — | — |
| Plantacare ® PS 10 Sodium Laureth Sulfate (and) Coco Glucosides | 22.0 | — | 5.0 | 22.0 | — | — | — | — | — | — |
| Dehyton ® PK 45 Cocamidopropyl Betaine | 15.0 | 10.0 | 15.0 | 15.0 | 20.0 | — | — | — | — | — |
| Emulgade ® SE Glyceryl Sterate (and) Ceteareth 12/20 (and) Cetearyl Alcohol (and) Cetyl Palmitate | — | — | — | — | — | 5.0 | 5.0 | 4.0 | — | — |
| Eumulgin ® B1 Ceteareth-12 | — | — | — | — | — | — | — | 1.0 | — | — |
| Lameform ® TGI Polyglyceryl-3 Isostearate | — | — | — | — | — | — | — | — | 4.0 | — |
| Dehymuls ® PGPH Polyglyceryl-2 Dipolyhydroxystearate | — | — | — | — | — | — | — | — | — | 4.0 |
| Monomuls ® 90-O 18 Glyceryl Oleate | — | — | — | — | — | — | — | — | 2.0 | — |
| Cetiol ® HE PEG-7 Glyceryl Cocoate | 2.0 | — | — | 2.0 | 5.0 | — | — | — | — | 2.0 |
| Cetiol ® OE Dicaprylyl Ether | — | — | — | — | — | — | — | — | 5.0 | 6.0 |
| Cetiol ® PGL Hexyldecanol (and) Hexyldecyl Laurate | — | — | — | — | — | — | — | 3.0 | 10.0 | 9.0 |
| Cetiol ® SN Cetearyl Isononanoate | — | — | — | — | — | 3.0 | 3.0 | — | — | — |
| Cetiol ® V Decyl Oleate | — | — | — | — | — | 3.0 | 3.0 | — | — | — |
| Myritol ® 318 Coco Caprylate Caprate | — | — | — | — | — | — | — | 3.0 | 5.0 | 5.0 |
| Bees Wax | — | — | — | — | — | — | — | — | 7.0 | 5.0 |
| Nutrilan ® Elastin E20 Hydrolyzed Elastin | — | — | — | — | — | 2.0 | — | — | — | — |
| Nutrilan ® I-50 Hydrolyzed Collagen | — | — | — | 2.0 | — | 2.0 | — | — | — | — |
| Gluadin ® AGP Hydrolyzed Wheat Gluten | 0.5 | 0.5 | 0.5 | — | — | — | 0.5 | — | — | — |

TABLE 4-continued

Examples of cosmetic compositions (water, preservatives ad 100% by weight)

| | | | | | | | | | | |
|---|---|---|---|---|---|---|---|---|---|---|
| Gluadin ® WK<br>Sodium Cocoyl<br>Hydrolyzed Wheat Protein | 2.0 | 2.0 | 2.0 | 2.0 | 5.0 | — | — | — | 0.5 | 0.5 |
| Euperlan ® PK 3000 AM<br>Glycol Distearate (and)<br>Laureth-4 (and)<br>Cocamidopropyl Betaine | 5.0 | — | — | 5.0 | — | — | — | — | — | — |
| Arlypon ® F<br>Laureth-2 | — | — | — | — | — | — | — | — | — | — |
| Retinol-Nanocapsules according to Exampl 3 | 1.0 | 1.0 | 1.0 | 1.0 | 1.0 | 1.0 | 1.0 | 1.0 | 1.0 | 1.0 |
| Hydagen ® CMF<br>Chitosan | 1.0 | 1.0 | 1.0 | 1.0 | 1.0 | 1.0 | 1.0 | 1.0 | 1.0 | 1.0 |
| Menthofuran/Frescolat MGA (1:1) | 0.3 | 0.3 | 0.3 | 0.3 | 0.3 | 0.3 | 0.3 | 0.3 | 0.3 | 0.3 |
| Glycerol (86% by weight) | — | — | — | — | — | 3.0 | 3.0 | 5.0 | 5.0 | 3.0 |

| Composition (INCI) | 31 | 32 | 33 | 34 | 35 | 36 | 37 | 38 | 39 | 40 |
|---|---|---|---|---|---|---|---|---|---|---|
| Dehymuls ® PGPH<br>Polyglyceryl-2<br>Dipolyhydroxystearate | 4.0 | 3.0 | — | 5.0 | — | — | — | — | — | — |
| Lameform ® TGI<br>Polyglyceryl-3<br>Diisostearate | 2.0 | 1.0 | — | — | — | — | — | — | — | — |
| Emulgade ® PL 68/50<br>Cetearyl Glucoside (and) Cetearyl Alcohol | — | — | — | — | 4.0 | — | — | — | 3.0 | — |
| Eumulgin ® B2<br>Ceteareth-20 | — | — | — | — | — | — | — | 2.0 | — | — |
| Tegocare ® PS<br>Polyglyceryl-3<br>Methylglucose Distearate | — | — | 3.0 | — | — | — | 4.0 | — | — | — |
| Eumulgin VL 75<br>Polyglyceryl-2<br>Dipolyhydroxystearate (and) Lauryl Glucoside (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS<br>Glyceryl Stearate | — | — | — | — | — | 2.0 | 4.0 | — | — | 4.0 |
| Lanette ® O<br>Cetearyl Alcohol | — | — | 2.0 | — | 2.0 | 4.0 | 2.0 | 4.0 | 4.0 | 1.0 |
| Antaron ® V 216<br>PVP/Hexadecene Copolymer | — | — | — | — | — | 3.0 | — | — | — | 2.0 |
| Myritol ® 818<br>Cocoglycerides | 5.0 | — | 10.0 | — | 8.0 | 6.0 | 6.0 | — | 5.0 | 5.0 |
| Finsolv ® TN<br>C12/15 Alkyl Benzoate | — | 6.0 | — | 2.0 | — | — | 3.0 | — | — | 2.0 |
| Cetiol ® J 600<br>Oleyl Erucate | 7.0 | 4.0 | 3.0 | 5.0 | 4.0 | 3.0 | 3.0 | — | 5.0 | 4.0 |
| Cetiol ® OE<br>Dicaprylyl Ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL<br>Hexadecanol (and) Hexyldecyl Laurate | — | 7.0 | 3.0 | 7.0 | 4.0 | — | — | — | 1.0 | — |
| Bisabolol | 1.2 | 1.2 | 1.2 | 1.2 | 1.2 | 1.2 | 1.2 | 1.2 | 1.2 | 1.2 |
| Menthofuran/Frescolat MGA (1:1) | 0.3 | 0.3 | 0.3 | 0.3 | 0.3 | 0.3 | 0.3 | 0.3 | 0.3 | 0.3 |
| Hydagen ® CMF<br>Chitosan | 1.0 | 1.0 | 1.0 | 1.0 | 1.0 | 1.0 | 1.0 | 1.0 | 1.0 | 1.0 |
| Copherol ® F 1300<br>Tocopherol/Tocopheyl Acetate | 0.5 | 1.0 | 1.0 | 2.0 | 1.0 | 1.0 | 1.0 | 2.0 | 0.5 | 2.0 |
| Neo Heliopan ® Hydro<br>Sodium Phenylbenzimidazole Sulfonate | 3.0 | — | — | 3.0 | — | — | 2.0 | — | 2.0 | — |
| Neo Heliopan ® 303<br>Octocrylene | — | 5.0 | — | — | — | 4.0 | 5.0 | — | — | 10.0 |
| Neo Heliopan ® BB<br>Benzophenone-3 | 1.5 | — | — | 2.0 | 1.5 | — | — | — | 2.0 | — |

TABLE 4-continued

| Examples of cosmetic compositions (water, preservatives ad 100% by weight) | | | | | | | | | | |
|---|---|---|---|---|---|---|---|---|---|---|
| Neo Heliopan ® E 1000 Isoamyl p-Methoxycinnamate | 5.0 | — | 4.0 | — | 2.0 | 2.0 | 4.0 | 10.0 | — | — |
| Neo Heliopan ® AV Octyl Methoxycinnamate | 4.0 | — | 4.0 | 3.0 | 2.0 | 3.0 | 4.0 | — | 10.0 | 2.0 |
| Uvinul ® T 150 Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | — | — | — | — | — | — | 5.0 | — | — |
| Glycerin (86 Gew.-% ig) | 5.0 | 5.0 | 5.0 | 5.0 | 5.0 | 5.0 | 5.0 | 5.0 | 5.0 | 5.0 |

(1-4) conditioner, (5-6) deep conditioner, (7-8) shower bath, (9) shower gel, (10) body wash (11-14) shower bath "Two-in-One"), (15-20) shampoo (21-25) foam bath, (26) soft cream, (27, 28) moisturizing emulsion, (29, 30) night cream (31) W/O sun screen cream, (32-34) W/O sun screen lotion, (35, 38, 40) O/W sun screen lotion (36, 37, 39) O/W sun screen cream Examples 15 to 21, Comparison Example V9

To determine the reduction of apatite solubility, firstly, a blind experiment was carried out. To this end, 300 ml desalinated water was thermostated at 37° C. in a reaction container. 0.5 g hydroxyl apatite powder (specific surface 60 m²/g, Merck) was suspended. The pH value of the suspension was maintained at a constant value of 5 by means of an automatic burette, by which lactic acid solution could be added. The amount of 0.1 molar lactic acid used for pH stabilisation was registered. The consumption of lactic acid registered after 2 hours corresponded to the solubility of untreated hydroxyl apatite powder ($L_u$).

Subsequently, the experiment was repeated, adding 50 mg and, respectively, 150 mg of the agent mixtures to be analysed. The consumption of lactic acid registered after 2 hours corresponded to the solubility of the treated hydroxyl apatite powder ($L_b$). The reduction of apatite solubility (ALR in %) by means of the active agent was calculated according to:

$ALR(\%)=(L_u-L_b)*100/L_u(\%)$

The results of the measurements are summarized in Table 5.

To determine the inhibition of crystal growth (CGI in %) of hydroxyl apatite, firstly, there was also carried out a blind experiment. To this end, 400 ml of a 0.0008 molar solution of $KH_2PO_4$ and 45 ml of a 0.012 molar solution of $CaCl_2$ were mixed in a reaction container. This solution was adjusted to a pH value of 7.4 by titration with a 0.05 molar solution of KOH. After a stable pH value was obtained for at least 30 minutes, 100 mg of hydroxyl apatite powder (specific surface 60 m²/g, Merck) were added. The pH value of the suspension was maintained at a constant value of 7.4 by means of an automatic burette, by which 0.05 molar solution of KOH could be added. The amount of 0.05 molar solution of KOH consumed for pH stabilisation was registered. The consumption of KOH solution ($K_u$) registered after 2 hours corresponded to the formation of hydroxyl apatite (growth of crystals in the suspension).

Subsequently, this experiment was repeated, adding 6 and, respectively, 30 mg of the active agent to be examined. The consumption of 0.05 molar solution of KOH ($K_b$) registered after 2 hours corresponded to the formation of hydroxyl apatite (growth of crystals in the suspension) under the influence of the active agent. The inhibition of crystal growth by the active agent is calculated according to:

$KWI(\%)=(K_u-K_b)*100/K_u(\%)$

The results of the measurements are summarized in Table 5.

TABLE 5

| Apatite solubility and inhibition of crystal growth depending on the aroma component | | | | | | | | |
|---|---|---|---|---|---|---|---|---|
| Composition | V9 | 15 | 16 | 17 | 18 | 19 | 20 | 21 |
| Aroma component | | | | | | | | |
| Menthol | | | | 60 | | | | |
| Menthone | | | | 25 | | | | |
| Methylacetat | | | | 5 | | | | |
| Neomenthol | 4 | 3 | 3 | 3 | 3 | 3 | 3 | 3 |
| Isomenthol | 4 | 3 | 3 | 3 | 3 | 3 | 3 | 3 |
| Menthofuran | 2 | 2 | 2 | 2 | 2 | 2 | 2 | 2 |
| Methyl Lactate | — | 2 | — | — | — | — | — | — |
| Menthone Glyceryl Acetal | — | — | 2 | — | — | — | — | — |
| Menthol Ethylen Glycol Carbonate | — | — | — | 2 | — | — | — | — |
| Menthol Propylen Glycol Carbonate | — | — | — | — | 2 | — | — | — |
| Menthyl Succinate | — | — | — | — | — | 2 | — | — |
| Menthyl Glutamate | — | — | — | — | — | — | 2 | — |
| WS-5 | — | — | — | — | — | — | — | 2 |
| Water | | | | Ad 100 | | | | |
| Apatite solubility [%] | | | | | | | | |
| 30 mg | 2 | 11 | 10 | 9 | 8 | 9 | 10 | 10 |
| 150 mg | 12 | 26 | 21 | 20 | 20 | 20 | 21 | 22 |

TABLE 5-continued

Apatite solubility and inhibition of crystal growth depending on the aroma component

| Composition | V9 | 15 | 16 | 17 | 18 | 19 | 20 | 21 |
|---|---|---|---|---|---|---|---|---|
| Inhibition of crystal growth [%] | | | | | | | | |
| 5 mg | 3 | 19 | 17 | 15 | 16 | 16 | 16 | 17 |
| 6 mg | 14 | 36 | 30 | 31 | 29 | 30 | 31 | 31 |

Examples 15 to 21 show that the compositions in accordance with the invention—in comparison with an aroma mixture, which corresponds to conventional peppermint oil—possess a clearly higher apatite solubility and a stronger inhibition of apatite crystal formation. Oral and dental cleaning agents comprising such measures feature an improved effect against the formation of calculus.

The following Table 6 contains a number of formulation examples for tooth pastes and mouthwashs.

TABLE 6

| Component | Commercial product | Amount [% by weight] |
|---|---|---|
| a Composition of the tooth paste | | |
| Precipitation silica | Sident ® 12 DS | 18.0 |
| Thickener silica | Aerosil ® 200 | 0.8 |
| Sorbit | | 17.5 |
| Glycerin | | 17.5 |
| Carboxymethylcellulose | Relatin ® 100 SR | 0.9 |
| Sodium lauryl sulfate | Texapon ® K1296 | 2.0 |
| Sodium fluoride | | 0.22 |
| Saccharin-sodium | | 0.2 |
| Aroma mixture | | 1.0 |
| Water | | Ad 100 |
| b Composition of the mouthwash | | |
| Ethanol (96% ig) | | 10.0 |
| Sorbitanmonolaurat + 20EO | Tween ® 20 | 0.4 |
| Aroma mixture | | 0.3 |
| Sorbit (70% aqueous solution) | | 8.0 |
| p-hydroxybenzoic acid methyl ester | | 0.2 |
| Water | | Ad 100 |

The following Table 7, lastly, shows a number of example formulations of chewing gum materials.

TABLE 7

Chewing gum materials

| Composition | A | B | C | D | E | F | G | H |
|---|---|---|---|---|---|---|---|---|
| Polyisobutylen (MW 20.000) | 30.0 | 30.0 | 30.0 | 40.0 | 20.0 | 20.0 | 25.0 | 30.0 |
| Glucose | 51.0 | 51.0 | 51.0 | 42.5 | | | | |
| Corn syrup | 10.0 | 10.0 | 10.0 | 8.0 | | | | |
| Sorbitol | | | | | 51.0 | 51.0 | 47.5 | 44.5 |
| Mannitol | | | | | 5.0 | 5.0 | 4.3 | 3.6 |
| Glycerol | 1.8 | 1.8 | 1.8 | 1.8 | 8.0 | 8.0 | 8.0 | 7.0 |
| Lycasin: Glycerol (1:1) | | | | | 8.2 | 8.2 | 8.0 | 7.0 |
| Lecithin | | | | | 0.2 | 0.2 | 0.2 | 0.2 |
| Aroma mixture | 1.0 | 1.0 | 1.0 | 1.0 | 1.0 | 1.0 | 1.0 | 1.0 |
| Water | | | | Ad 100 | | | | |

The invention claimed is:

1. A composition, comprising
   (a) menthofuran, and
   (b) menthol compounds corresponding to the formulas (I), (II) and/or (III)

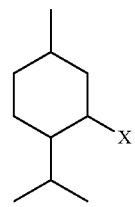

(I)

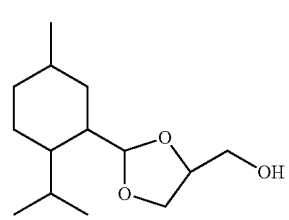

(II)

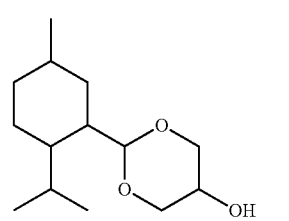

(III)

in which X represents —OY or —COZ and Y represents the following groups:
   (i) a linear or branched alkyl or hydroxyalkyl radical containing 1 to 6 carbon atoms or an allyl radical;
   (ii) a hydroxyl or dihydroxy alkyl radical containing 1 to 6 carbon atoms;
   (iii) a radical —OCR$^1$;
   (iv) a radical —OCO(M)OH;
   (v) a radical —OCO—S;
   (vi) a radical —OC(CH$_2$)$_n$COR$^2$,
wherein
M represents a linear or branched alkyl or alkenyl containing 1 to 10 carbon atoms;
S represents a carbohydrate radical containing 5 to 12 carbon atoms;
n stands for 0 or numbers of 1 to 6;
R$^1$ represents a linear or branched alkyl or hydroxyalkyl radical containing 1 to 6 carbon atoms or an allyl radical;
R$^2$ represents a hydroxyl radical or a radical NR$^3$R$^4$;

R³ and R⁴ represent, independently from one another, hydrogen or a linear or branched alkyl or hydroxyalkyl radical containing 1 to 6 carbon atoms,
while Z represents the following groups:
(vii) a radical $NR^5R^6$, or
(viii) a radical $NHR^7$,
R⁵ and R⁶ represent, independently from one another, hydrogen or a linear or branched alkyl and/or hydroxyalkyl radical containing 1 to 6 carbon atoms, a phenyl radical or an alkoxyphenyl radical containing 1 to 6 carbon atoms in the alkoxy radical,
R⁷ represents a radical —$(CH_2)_n COOR^8$,
R⁸ represents a linear or branched alkyl or hydroxyalkyl radical containing 1 to 6 carbon atoms, and
n stands for 0 or numbers of 1 to 10 wherein components (a) and (b) are present in the weight ratio of from 40:60 to 60:40.

2. The composition of claim 1, comprising, as component (b) menthol compounds selected from the group consisting of menthol methyl ether, menthone glyceryl acetal (FEMA GRAS 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamat, monomethyl succinate (FEMA GRAS 3810), monomenthyl glutamate (FEMA GRAS 4006), menthoxy-1, 2-propanediol (FEMA GRAS 3784), menthoxy-2-methyl-1, 2-propandiol (FEMA GRAS 3849) and the menthan carboxylic acid esters and amides WS-3, WS-4, WS-5, WS-12, WS-14 and WS-30 and the mixtures thereof.

3. The composition of claim 1, additionally comprising a cosmetic additive (component c), which is selected from the group consisting of surfactants, oil bodies, emulsifiers, pearlizing waxes, consistency factors, thickeners, superfatting agents, stabilizers, polymers, silicon compounds, fats, waxes, lecithins, phospholipids, UV protection factors, moisturizers, biogenic agents, antioxidants, deodorants, antiperspirants, anti-dandruff agents, film formers, swelling agents, insect repellants, self-tanning agents, tyrosine inhibitors depigmenting agents, hydrotropes, solubilizers, preservatives, perfume oils and dyes and the mixtures thereof.

4. The composition of claim 3, wherein components (a+b) and (c) are present in the weight ratio of from 0.01:99.9 to 2:98.

5. The composition of claim 1 wherein the composition is a cosmetic composition, comprising
(a) menthofuran,
(b) menthol compounds corresponding to the formulas (I), (II) and/or (III), and
(c) a carrier for cosmetic applications.

6. The cosmetic composition of claim 5, wherein the carrier is selected from the group consisting of water, alcohols containing 2 to 6 carbon atoms, polyols containing 1 to 10 carbon atoms and 2 to 4 hydroxyl groups and oil bodies.

7. The cosmetic composition of claim 5, selected from the group consisting of skin care products, hair care products, sun screen products and oral and dental care products.

8. The composition of claim 1 wherein the composition is a pharmaceutical composition, comprising
(a) menthofuran,
(b) menthol compounds corresponding to the formulas (I), (II) and/or (III), and
(c) a carrier for pharmaceutical applications,
for treatment of cold symptoms.

9. The pharmaceutical composition of claim 8, wherein the carrier is selected from the group consisting of water, alcohols containing 2 to 6 carbon atoms, polyols containing 1 to 10 carbon atoms and 2 to 4 hydroxyl groups and oil bodies.

10. The pharmaceutical composition of claim 8, selected from the group consisting of lozenges, cold drops, syrups, cold balms and cold sprays.

11. The composition of claim 1 wherein the composition is a food composition, comprising
(a) menthofuran,
(b) menthol compounds corresponding to the formulas (I), (II) and/or (III), and
(c) a carrier for food.

12. The food composition of claim 11, wherein the carrier is selected from the group consisting of water, ethanol and glycerol.

13. The food composition of claim 11, selected from the group consisting of beverages, milk products, bakery products, chewing gums and bonbons.

* * * * *